United States Patent
Bender et al.

(10) Patent No.: US 9,204,836 B2
(45) Date of Patent: Dec. 8, 2015

(54) SPORADIC COLLECTION OF MOBILE AFFECT DATA

(71) Applicant: Affectiva, Inc., Waltham, MA (US)

(72) Inventors: Daniel Bender, Cambridge, MA (US); Rana el Kaliouby, Boston, MA (US); Evan Kodra, Waltham, MA (US); Oliver Ernst Nowak, Medford, MA (US); Richard Scott Sadowsky, Sturbridge, MA (US)

(73) Assignee: Affectiva, Inc., Waltham, MA (US)

( * ) Notice: Subject to any disclaimer, the term of this patent is extended or adjusted under 35 U.S.C. 154(b) by 2 days.

(21) Appl. No.: 14/064,136

(22) Filed: Oct. 26, 2013

(65) Prior Publication Data

US 2014/0051047 A1    Feb. 20, 2014

Related U.S. Application Data

(63) Continuation-in-part of application No. 13/153,745, filed on Jun. 6, 2011.

(60) Provisional application No. 61/719,383, filed on Oct. 27, 2012, provisional application No. 61/747,651,
(Continued)

(51) Int. Cl.
*G06K 9/00*      (2006.01)
*A61B 5/16*      (2006.01)
*G06F 19/00*     (2011.01)
(Continued)

(52) U.S. Cl.
CPC .............. *A61B 5/165* (2013.01); *A61B 5/0022* (2013.01); *G06F 19/3418* (2013.01); *G06F 19/3481* (2013.01); *A61B 5/0077* (2013.01); *A61B 5/02055* (2013.01); *A61B 5/02405* (2013.01); *A61B 5/0531* (2013.01); *A61B 5/0533* (2013.01); *A61B 5/08* (2013.01); *A61B 5/11* (2013.01); *A61B 5/6898* (2013.01); *A61B 5/72* (2013.01); *G06Q 30/0271* (2013.01)

(58) Field of Classification Search
None
See application file for complete search history.

(56) References Cited

U.S. PATENT DOCUMENTS

| | | | |
|---|---|---|---|
| 3,034,500 A | 5/1962 | Backster, Jr. | |
| 3,548,806 A | 12/1970 | Fisher | |

(Continued)

FOREIGN PATENT DOCUMENTS

| | | |
|---|---|---|
| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.

(Continued)

*Primary Examiner* — Wesley Tucker
(74) *Attorney, Agent, or Firm* — Adams Intellex, PLC

(57) ABSTRACT

A user may react to an interaction by exhibiting a mental state. A camera or other monitoring device can be used to capture one or more manifestations of the user's mental state, such as facial expressions, electrodermal activity, or movements. However, there may be conditions where the monitoring device is not able to detect the manifestation continually. Thus, various capabilities and implementations are described where the mental state data is collected on an intermittent basis, analyzed, and an output rendered based on the analysis of the mental state data.

22 Claims, 6 Drawing Sheets

Related U.S. Application Data filed on Dec. 31, 2012, provisional application No. 61/747,810, filed on Dec. 31, 2012, provisional application No. 61/793,761, filed on Mar. 15, 2013, provisional application No. 61/790,461, filed on Mar. 15, 2013, provisional application No. 61/789,038, filed on Mar. 15, 2013, provisional application No. 61/798,731, filed on Mar. 15, 2013, provisional application No. 61/844,478, filed on Jul. 10, 2013, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011.

(51) Int. Cl.
| | |
|---|---|
| A61B 5/053 | (2006.01) |
| A61B 5/00 | (2006.01) |
| A61B 5/0205 | (2006.01) |
| A61B 5/024 | (2006.01) |
| A61B 5/08 | (2006.01) |
| A61B 5/11 | (2006.01) |
| G06Q 30/02 | (2012.01) |

(56) References Cited

U.S. PATENT DOCUMENTS

| | | | |
|---|---|---|---|
| 3,870,034 | A | 3/1975 | James |
| 4,353,375 | A | 10/1982 | Colburn et al. |
| 4,448,203 | A | 5/1984 | Williamson et al. |
| 4,794,533 | A | 12/1988 | Cohen |
| 4,807,642 | A | 2/1989 | Brown |
| 4,817,628 | A | 4/1989 | Zealear et al. |
| 4,950,069 | A | 8/1990 | Hutchinson |
| 4,964,411 | A | 10/1990 | Johnson et al. |
| 5,016,282 | A | 5/1991 | Tomono et al. |
| 5,031,228 | A | 7/1991 | Lu |
| 5,219,322 | A | 6/1993 | Weathers |
| 5,247,938 | A | 9/1993 | Silverstein et al. |
| 5,259,390 | A | 11/1993 | MacLean |
| 5,507,291 | A | 4/1996 | Stirbl et al. |
| 5,572,596 | A | 11/1996 | Wildes et al. |
| 5,619,571 | A | 4/1997 | Sandstrom et al. |
| 5,647,834 | A | 7/1997 | Ron |
| 5,649,061 | A | 7/1997 | Smyth |
| 5,663,900 | A | 9/1997 | Bhandari et al. |
| 5,666,215 | A | 9/1997 | Fredlund et al. |
| 5,676,138 | A * | 10/1997 | Zawilinski ............ 600/301 |
| 5,725,472 | A | 3/1998 | Weathers |
| 5,741,217 | A | 4/1998 | Gero |
| 5,760,917 | A | 6/1998 | Sheridan |
| 5,762,611 | A | 6/1998 | Lewis et al. |
| 5,772,591 | A | 6/1998 | Cram |
| 5,774,591 | A | 6/1998 | Black et al. |
| 5,802,220 | A | 9/1998 | Black et al. |
| 5,825,355 | A | 10/1998 | Palmer et al. |
| 5,886,683 | A | 3/1999 | Tognazzini et al. |
| 5,898,423 | A | 4/1999 | Tognazzini et al. |
| 5,920,477 | A | 7/1999 | Hoffberg et al. |
| 5,945,988 | A | 8/1999 | Williams et al. |
| 5,959,621 | A | 9/1999 | Nawaz et al. |
| 5,969,755 | A | 10/1999 | Courtney |
| 5,983,129 | A | 11/1999 | Cowan et al. |
| 5,987,415 | A | 11/1999 | Breese et al. |
| 6,004,061 | A | 12/1999 | Manico et al. |
| 6,004,312 | A | 12/1999 | Finneran et al. |
| 6,008,817 | A | 12/1999 | Gilmore, Jr. |
| 6,026,321 | A | 2/2000 | Miyata et al. |
| 6,026,322 | A | 2/2000 | Korenman et al. |
| 6,056,781 | A | 5/2000 | Wassick et al. |
| 6,067,565 | A | 5/2000 | Horvitz |
| 6,088,040 | A | 7/2000 | Oda et al. |
| 6,099,319 | A | 8/2000 | Zaltman et al. |
| 6,134,644 | A | 10/2000 | Mayuzumi et al. |
| 6,182,098 | B1 | 1/2001 | Selker |
| 6,185,534 | B1 | 2/2001 | Breese et al. |
| 6,195,651 | B1 | 2/2001 | Handel et al. |
| 6,212,502 | B1 | 4/2001 | Ball et al. |
| 6,222,607 | B1 | 4/2001 | Szajewski et al. |
| 6,309,342 | B1 | 10/2001 | Blazey et al. |
| 6,327,580 | B1 | 12/2001 | Pierce et al. |
| 6,349,290 | B1 | 2/2002 | Horowitz et al. |
| 6,351,273 | B1 | 2/2002 | Lemelson et al. |
| 6,437,758 | B1 | 8/2002 | Nielsen et al. |
| 6,443,840 | B2 | 9/2002 | Von Kohorn |
| 6,530,082 | B1 | 3/2003 | Del Sesto et al. |
| 6,577,329 | B1 | 6/2003 | Flickner et al. |
| 6,629,104 | B1 | 9/2003 | Parulski et al. |
| 6,792,458 | B1 | 9/2004 | Muret et al. |
| 6,847,376 | B2 | 1/2005 | Engeldrum et al. |
| 7,013,478 | B1 | 3/2006 | Hendricks et al. |
| 7,113,916 | B1 | 9/2006 | Hill |
| 7,120,880 | B1 | 10/2006 | Dryer et al. |
| 7,197,459 | B1 | 3/2007 | Harinarayan et al. |
| 7,233,684 | B2 | 6/2007 | Fedorovskaya et al. |
| 7,246,081 | B2 | 7/2007 | Hill |
| 7,263,474 | B2 | 8/2007 | Fables et al. |
| 7,266,582 | B2 | 9/2007 | Stelting |
| 7,307,636 | B2 | 12/2007 | Matraszek et al. |
| 7,327,505 | B2 | 2/2008 | Fedorovskaya et al. |
| 7,350,138 | B1 | 3/2008 | Swaminathan et al. |
| 7,353,399 | B2 | 4/2008 | Ooi et al. |
| 7,355,627 | B2 | 4/2008 | Yamazaki et al. |
| 7,428,318 | B1 | 9/2008 | Madsen et al. |
| 7,474,801 | B2 | 1/2009 | Teo et al. |
| 7,496,622 | B2 | 2/2009 | Brown et al. |
| 7,549,161 | B2 | 6/2009 | Poo et al. |
| 7,551,755 | B1 | 6/2009 | Steinberg et al. |
| 7,555,148 | B1 | 6/2009 | Steinberg et al. |
| 7,558,408 | B1 | 7/2009 | Steinberg et al. |
| 7,564,994 | B1 | 7/2009 | Steinberg et al. |
| 7,573,439 | B2 | 8/2009 | Lau et al. |
| 7,580,512 | B2 | 8/2009 | Batni et al. |
| 7,584,435 | B2 | 9/2009 | Bailey et al. |
| 7,587,068 | B1 | 9/2009 | Steinberg et al. |
| 7,610,289 | B2 | 10/2009 | Muret et al. |
| 7,620,934 | B2 | 11/2009 | Falter et al. |
| 7,644,375 | B1 | 1/2010 | Anderson et al. |
| 7,676,574 | B2 | 3/2010 | Glommen et al. |
| 7,826,657 | B2 | 11/2010 | Zhang et al. |
| 7,830,570 | B2 | 11/2010 | Morita et al. |
| 7,921,036 | B1 | 4/2011 | Sharma |
| 8,010,458 | B2 | 8/2011 | Galbreath et al. |
| 8,401,248 | B1 | 3/2013 | Moon et al. |
| 2001/0033286 | A1 | 10/2001 | Stokes et al. |
| 2001/0041021 | A1 | 11/2001 | Boyle et al. |
| 2002/0007249 | A1 | 1/2002 | Cranley |
| 2002/0030665 | A1 | 3/2002 | Ano |
| 2002/0042557 | A1 | 4/2002 | Bensen et al. |
| 2002/0054174 | A1 | 5/2002 | Abbott et al. |
| 2002/0084902 | A1 | 7/2002 | Zadrozny et al. |
| 2002/0171551 | A1 * | 11/2002 | Eshelman et al. ........ 340/573.1 |
| 2002/0182574 | A1 | 12/2002 | Freer |
| 2003/0035567 | A1 | 2/2003 | Chang et al. |
| 2003/0037041 | A1 | 2/2003 | Hertz |
| 2003/0078513 | A1 | 4/2003 | Marshall |
| 2003/0093784 | A1 * | 5/2003 | Dimitrova et al. ............ 725/10 |
| 2003/0191682 | A1 | 10/2003 | Shepard et al. |
| 2004/0181457 | A1 | 9/2004 | Biebesheimer et al. |
| 2005/0187437 | A1 * | 8/2005 | Matsugu et al. ............ 600/301 |
| 2005/0289582 | A1 | 12/2005 | Tavares et al. |
| 2006/0019224 | A1 | 1/2006 | Behar et al. |
| 2006/0115157 | A1 | 6/2006 | Mori |
| 2006/0235753 | A1 | 10/2006 | Kameyama |
| 2007/0255831 | A1 | 11/2007 | Hayashi et al. |
| 2007/0299964 | A1 | 12/2007 | Wong et al. |
| 2008/0091512 | A1 | 4/2008 | Marci et al. |

(56) References Cited

U.S. PATENT DOCUMENTS

| | | |
|---|---|---|
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0208015 A1 | 8/2008 | Morris et al. |
| 2009/0006206 A1 | 1/2009 | Groe et al. |
| 2009/0083421 A1 | 3/2009 | Glommen et al. |
| 2009/0094286 A1 | 4/2009 | Lee et al. |
| 2009/0133048 A1 | 5/2009 | Gibbs et al. |
| 2009/0150919 A1 | 6/2009 | Lee et al. |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1* | 10/2010 | Anderson et al. .............. 709/203 |
| 2011/0092780 A1 | 4/2011 | Zhang et al. |
| 2011/0126226 A1 | 5/2011 | Makhlouf |
| 2011/0143728 A1 | 6/2011 | Holopainen et al. |
| 2011/0196855 A1 | 8/2011 | Wable et al. |
| 2011/0231240 A1 | 9/2011 | Schoen et al. |
| 2011/0263946 A1 | 10/2011 | El Kaliouby et al. |
| 2012/0304206 A1 | 11/2012 | Roberts et al. |

FOREIGN PATENT DOCUMENTS

| | | |
|---|---|---|
| KR | 10-2008-0016303 A | 2/2008 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

International Search Report dated Nov. 14, 2011 for PCT/US2011/039282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

* cited by examiner

SPORADIC COLLECTION OF MOBILE AFFECT DATA

RELATED APPLICATIONS

This application claims the benefit of U.S. provisional patent applications "Sporadic Collection of Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013. This application is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to analysis of non-continuous collection of mental states.

BACKGROUND

People increasingly spend a tremendous amount of time interacting with computers; this interaction includes a copious amount of media consumption using these computers. This interaction may be for many different reasons such as education, entertainment, social media interaction, document creation, and gaming, to name a few.

In some cases the human-computer interaction can take the form of a person performing a task using a software-based tool running on a computer. Examples include filling out a tax form, creating a document, editing a video, and/or doing one or more of the numerous other activities performable by a modern computer. The person can find the execution of certain activities interesting or even exciting, and may be surprised at how easy it is to perform the activity. The person may become excited, happy, or content as he or she performs such an interesting or exciting activity. On the other hand, the person can find some activities difficult to perform, and may become frustrated or even angry with the computer or software tool. In some cases, users are surveyed in an attempt to determine where a computer or computer program may be functioning well, and where it may need improvement. However, such survey results are often unreliable because the surveys are often competed well after the activity was performed. In addition, survey participation rates may be low, and people may not provide accurate and honest answers to the survey.

In other cases of human-computer interaction, the person is using a software tool to accomplish a task, but instead may be consuming computer-accessed content or media such as news, pictures, music, or video. Currently, while or after consuming computer-driven content, viewers may tediously self-rate the media to communicate personal preferences. In some cases, viewers may enter a specific number of stars corresponding to a level of like or dislike, while in other cases, users may be asked to answer a list of questions. While this system of evaluation is a helpful metric to evaluate media and other products or services, such evaluation may be tedious and challenging. Thus, in many cases, this type of subjective evaluation is neither a reliable nor practical way to evaluate personal response to media. Recommendations based on such a system of star rating or other self-reporting are imprecise, subjective, unreliable, and are further limited by sample size: often, only a small number of viewers actually rate the media they have consumed.

SUMMARY

A user interacts with a computer and this interaction may entail one of a variety of tasks and/or activities. The user may react to the interaction with the reaction being a mental state. Such a mental state can express itself in one or more of many ways, such as facial expressions, electrodermal activity, movements, or other externally detectable manifestations. A camera or other monitoring device can be used to capture one or more of the externally detectable manifestations of the user's mental state, but there may be conditions where the monitoring device may not be able to detect the manifestation continually. Thus, various methods, computer program products, apparatus, and systems are described wherein mental state data is collected on an intermittent basis, analyzed, and an output rendered based on the analysis of the mental state data. A computer-implemented method for mental state analysis is disclosed comprising: collecting mental state data of an individual on an intermittent basis; obtaining analysis of the mental state data on the individual; and rendering an output based on the analysis of the mental state data. In embodiments, the method includes interpolation of mental state data or mental state analysis in between the collecting which is intermittent. In some embodiments, collecting other mental state data, including electrodermal activity, from the individual can occur on a continuous basis.

In embodiments, a computer implemented method for mental state analysis comprises: receiving mental state data collected from an individual on an intermittent basis; analyzing the mental state data from the individual; and sending an output related to analyzing that was performed. In some embodiments, a computer program product embodied in a non-transitory computer readable medium for mental state analysis comprises: code for collecting mental state data of an individual on an intermittent basis; code for obtaining analysis of the mental state data on the individual; and code for rendering an output based on the analysis of the mental state data. In embodiments, a system for mental state analysis may comprise: a memory for storing instructions; one or more processors attached to the memory wherein the one or more processors are configured to: collect mental state data of an individual on an intermittent basis; obtain analysis of the mental state data on the individual; and render an output based on the analysis of the mental state data.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
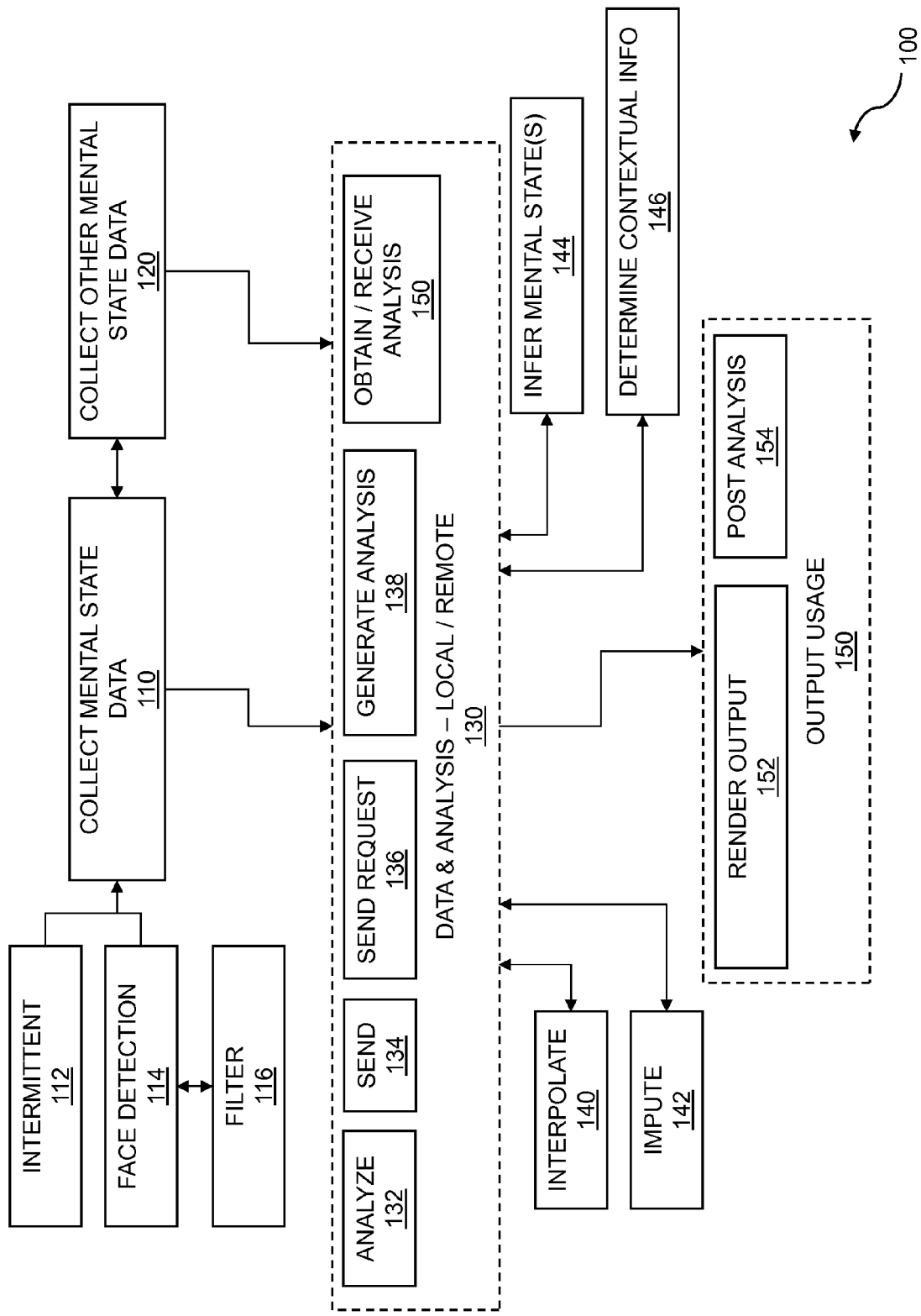
FIG. 1 is a flow diagram for sporadic collection.

As a user interacts with a computer, the user's mental state can provide valuable insight into the nature of the human-computer interaction. The mental state of the user can include such emotions as enjoyment, happiness, anger, sadness, stress, frustration, confusion, disappointment, hesitation, cognitive overload, fear, exhaustion, focus, engagement, attention, boredom, exploration, confidence, trust, delight, satisfaction, excitement, happiness, contentment, or one of many other human emotions. Understanding a user's mental state as he or she interacts with the computer may be valuable for a variety of reasons, such as determining which aspects of a computer program may be working well and which aspects need improvement, determining aspects of a computer game that may be too difficult or two easy for some users, measuring effectiveness of advertisements, determining which parts of a video most please a specific user, or determining a user's preferences in order to better suggest what other media, games, or applications the specific user may find appealing, just to name a few.

While consuming media, the user may exhibit physical manifestations of his or her mental state, such as facial expressions, physiological reactions, and movement. Sensors coupled to a computer—in some embodiments, the same computer the user is interacting with, in other embodiments, one or more other computers—may be able to detect, capture, and/or measure one or more external manifestations of the user's mental state. For example, a still camera may be able to capture images of the user's face, a video camera may be able to capture images of the user's movements, a heart rate monitor may be able to measure the user's heart rate, a skin resistance sensor may be able to detect changes in the user's galvanic skin response, and an accelerometer may be able to measure such movements as gestures, foot tapping, or head tilts, to name a few.

Depending on the user and/or the sensor, however, it may not be possible to continuously capture all of the manifestations of mental states under observation. For example, if the user looks away from the camera, it may not be possible to capture an image of their face until they look back at the camera. As a further example, a skin resistance sensor embedded in an armrest of the user's chair can only measure a galvanic skin response if the user's arm is resting on the armrest. In other cases, it may be possible to continuously capture the data from a sensor, but it may not be practical or desirable to do so due to the volume of data capture, or due to the relative slowness of measurable change that may be expected from the manifestation of a particular mental state.

To accommodate such circumstances, data from at least some of the sensors which measure manifestations of mental state (which may also be referred to as mental state data), such as data from a camera, biosensor, or accelerometer, may be captured, collected, and/or stored, on an intermittent basis. The intermittent basis may be sporadic, opportunistic, periodic, random, or any other non-continuous basis. Data from the sensors may be captured from the sensor based on the ability of the sensor to capture valid data, based on the usefulness of the data captured from the sensor, based on a schedule, or based on indications from other sensors, depending on the embodiment. For example, a skin resistance meter may only provide collectable data if it detects that the user's skin is in contact with the meter. Similarly, an image from a camera may be saved for further analysis perhaps only if some form of pre-processing detects that the user's face is visible in the image, or a video of a user's body (used for movement analysis) may be taken only when triggered by a change in heart rate detected by a heart rate monitor. A wide variety of techniques may be used to intermittently collect, capture, and/or store sensor data related to a mental state of an individual. In one example, when a pattern of motion predicts a high probability of a physiological condition occurring, other sensors may be activated to provide greater contextual information and increase predictive abilities.

Once the intermittent sensor data has been collected, an analysis of the mental state data collected from the sensors is obtained. The analysis may take place on the computer with which the user is interacting, the computer(s) that captured the sensor data, and/or from one or more other computers that may be local or remote to the user. The analysis may provide mental states of the user over time based on the sensor data. In some cases the mental state of the user may be estimated for the periods where data from one or more sensors was not collected.

After the analysis of the mental state data has been obtained, an output is rendered based on the analysis of the mental state data. The rendered output may include text, icons, pictures, graphs, binary data, or any other form or output that may be interpreted by a person or another computer, depending on the embodiment. In at least one embodiment, the rendered output may include a graph showing the prevalence of a particular mental state over time. In some embodiments, the rendered output may include an icon that changes based on the user's mental state. In some embodiments, the rendered output may include a file containing numerical data based on the analysis obtained. In embodiments, the sporadic collection of mental state data can be used in evaluating well-being of a person or in the generation of a personal emotional profile.

FIG. 1 is a flow diagram for sporadic collection. The flow 100 comprises a computer-implemented method for mental state analysis. The flow 100 includes collecting the mental state data 110 of an individual on an intermittent basis 112. Any non-continuous collection of mental state data may be considered collection on an intermittent basis 112, but in some embodiments the intermittent basis 112 may be opportunistic. That is, the intermittent basis 112 may either be sporadic or occasional; the intermittent basis 112 may mean the capture of images at random intervals or at times that the individual takes certain actions or happens to look at the camera. In other embodiments, the intermittent basis 112 can be periodic, and may occur on a regular schedule, such as once every 30 seconds. In some embodiments, the intermittent basis is a combination of occasional and periodic collection; for example, collecting mental state data once every minute plus additional collection each time the user clicks the mouse button or hits the 'Enter' key. The collecting may be accomplished for one type of mental state data and this mental state data may include facial data. In addition to the mental state data collected on an intermittent basis, the flow 100 may further comprise collecting other mental state data 120 from the individual on a continuous basis.

Many different types of mental state data may be collected. For example, the mental state data may include one or more of a group including physiological data, facial data, or accelerometer data. The collecting of the mental state data may be accomplished using a variety of different sensors, depending on the type of mental state data being collected, but in at least one embodiment, a camera coupled to the computer may be used to capture facial expression that may function as mental state data. Facial expressions that may function as mental state data may include one or more of smiles, laughter, smirks, or grimaces. The mental state data may also include one or more of head position, up/down head motion, side-to-side head motion, tilting head motion, body leaning motion, or gaze direction, which may be captured using a camera, an accelerometer, eye-tracking glasses, or other types of sensors. In some embodiments, the collecting of mental state data is accomplished with a mobile device in some embodiments. The flow 100 may include performing face detection 114 to determine when the individual is looking in the direction of a camera and may also include filtering out faces 116 of one or more other people to determine when the individual is looking in the direction of a camera.

In addition to collecting mental state data 110, the flow 100 includes data processing and analysis that may occur locally or remotely 130 from the individual. The flow 100 may further comprise analyzing 132 the mental state data to produce mental state information. In some embodiments, the analysis 132 of the mental state data may be performed locally, such as on the computer that is coupled to the sensors collecting the mental state data or on the computer with which the individual is interacting. The flow 100 may further comprise sending 134 one or more of the mental state data, a subset of the mental state data, or an initial analysis of the mental state data to a web service for further analysis, storage, or other purposes. The sending 134 may be accomplished on a periodic or an occasional basis, and may be sent using a different time basis than the one used in the data collection. So, for example, the mental state data may be collected on an opportunistic or random intermittent basis, but the mental state data may be sent on either a periodic or occasional basis. The flow 100 may further comprise sending a request 136 to a web service for the analysis or other activities related to the mental state data sent, and may include generating the analysis 138 by the web service through cloud computation. The flow 100 may include obtaining analysis 150 of the mental state data on the individual. This obtaining analysis 150 may include diverse methods, including, but not limited to, analyzing the mental state data locally, having the mental state data analyzed remotely, receiving an analysis of the mental state data directly from a smart sensor, or generating the analysis on a co-processor or dedicated subsystem.

The flow 100 may further comprise interpolating 140 mental state data in between the intermittent collecting. Interpolating 140 may be done using any suitable algorithm including piecewise constant interpolation, linear interpolation, polynomial interpolation, bicubic interpolation, a Gaussian process, one of the numerous and various curve fitting algorithms known in the art, or any other algorithm. In some embodiments, the interpolating 140 is of mental state analysis, in between the collecting which is intermittent. The flow 100 may include imputing 142 additional mental state data where the mental state data is missing. When the mental state data is collected 110 on an intermittent basis, there will be times when the mental state data is not collected and thus is missing. This missing mental state data may be imputed, or predicted, based on other data. The imputation may be based on other data collected from the individual on whom the data is missing. In other cases, the imputation may be based on mental state data collected from other individuals around the individual on whom the data is missing. These other individuals may be geographically nearby or may be part of the individual's social network. Thus, the missing mental state data may be imputed based on mental state data for other people in the individual's social network.

The flow 100 may further comprise inferring mental states 144 based on the mental state data which was collected. Mental states that may be inferred may include one or more of a group including enjoyment, happiness, anger, sadness, stress, frustration, confusion, disappointment, hesitation, cognitive overload, focusing, being engaged, attending, boredom, exploration, confidence, trust, delight, and satisfaction. The flow 100 may further comprise determining contextual information 146 which may be based on one or more of skin temperature or accelerometer data, or other types of data such as the application being used on the computer, the time of day, or any other type of contextual information.

The flow 100 may include output usage 150. An output may be rendered 152 based on the mental state data and/or the mental state. Depending on the embodiment, the output may include text, icons, pictures, graphs, binary data, or any other form or output that may be interpreted by a person or another computer. The rendered output may be used in various ways, including presenting the rendered output to the individual, storing the rendered output, sending the rendered output to a central collection point, or printing the rendered output. The flow 100 may further comprise posting the analysis 154 to a social network page. The posting to the social network page may be the rendered output or may be at least a portion of the mental state data or information regarding the mental state. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
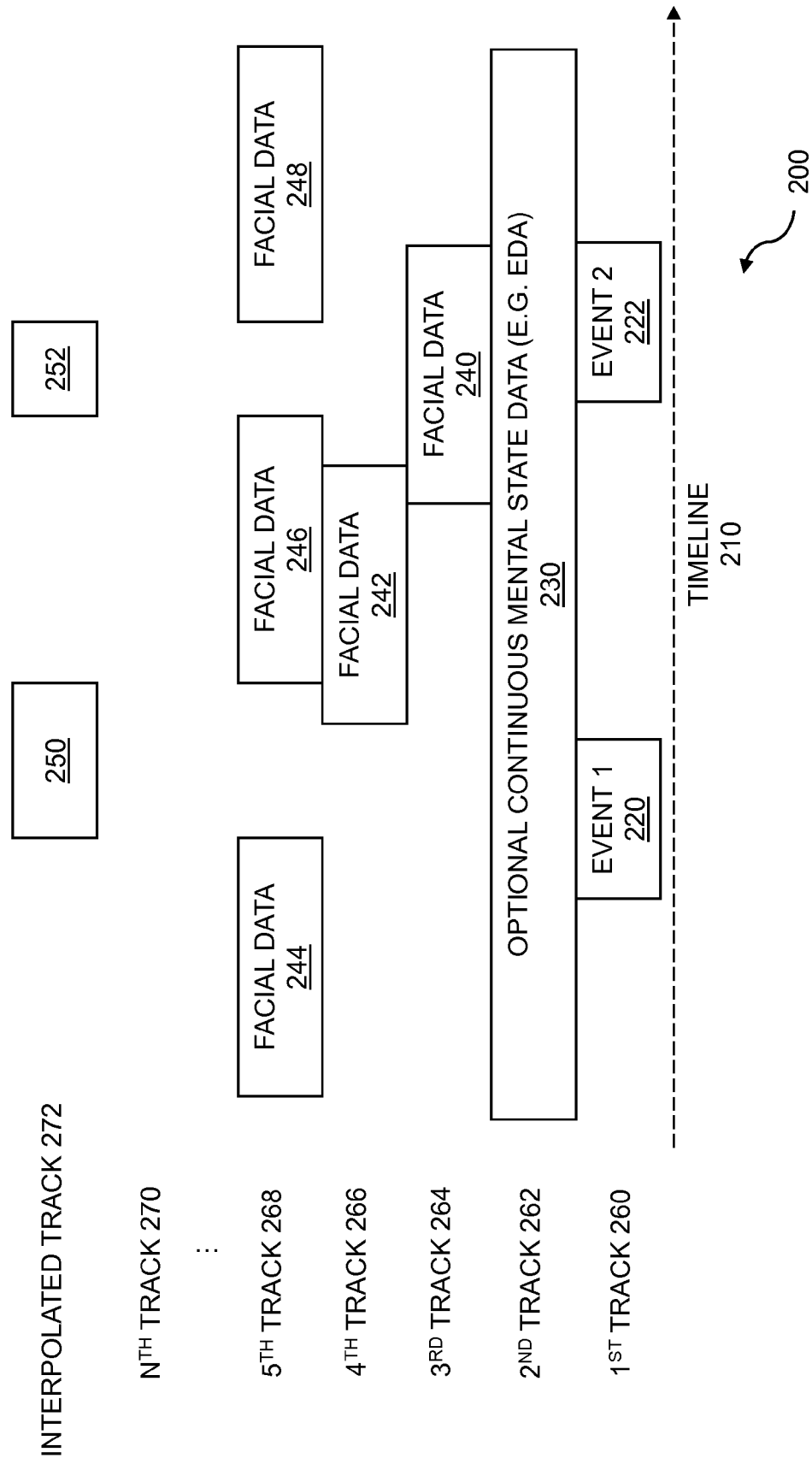
FIG. 2 is a timeline with information tracks relating to mental states.

FIG. 2 is a timeline 210 with information tracks 200 relating to mental states. A first track 260 shows events that may be related to the individual's use of a computer. A first event 220 may indicate an action that the individual took (such as launching an application); an action initiated by the computer (such as the presentation of a dialog box); an external event (such as a new global positioning system (GPS) coordinate); or receiving an e-mail, a phone call, a text message, or any other type of event. In some embodiments, a photograph may be used to document an event or simply save contextual information in the first track 260. A second event 222 may indicate another action or event. Such events may be used to provide contextual information and may also include such things as copies of emails, text messages, phone logs, file names, or other information that may be useful in understanding the context of a user's actions. Thus, in embodiments, contextual information is based on one or more of a photograph, an email, a text message, a phone log, or GPS information.

A second track 262 may include continuously collected mental state data such as electrodermal activity data 230. A third track 264 may include facial data 240, which may be a type of mental state data that is collected on an intermittent basis by a first camera, such as the room camera (although in some embodiments the facial data may be collected continuously). The facial data may be collected intermittently when the individual is looking toward a camera. The facial data 240 may include one or more still photographs, videos, or abstracted facial expressions which may be collected when the user looks in the direction of the camera. A fourth track 266 may include facial data 242 that is collected on an intermittent or continuous basis by a second camera, such as the mobile phone camera. The facial data 242 may include one or more still photographs, videos, or abstracted facial expressions which may be collected when the user looks in the direction of that camera. A fifth track 268 may include facial data that is collected from a third camera, such as the webcam. In the example shown, the fifth track 268 includes first facial data 244, second facial data 246, and third facial data 248 which may be any type of facial data including data that may be used for determining mental state information. Any number of samples of facial data may be collected in any track. The mental state data from the various tracks may be collected simultaneously, collected on one track exclusive of other tracks, collected where mental state data overlaps between the tracks, and so on. When mental state data from multiple tracks overlaps, one track's data may take precedence or the data from the multiple tracks may be combined.

Additional tracks, through the $n^{th}$ track 270, of mental state data of any type may be collected. The additional tracks 270 may be collected on a continuous or on an intermittent basis. The intermittent basis may be either occasional or periodic. Analysis may further comprise interpolating mental state data when the mental state data collected is intermittent, and/or imputing additional mental state data where the mental state data is missing. One or more interpolated tracks 272 may be included and may be associated with mental state data that is collected on an intermittent basis, such as the facial data of the fifth track 268. Interpolated data 250 and interpolated data 252 may contain interpolations of the facial data of the fifth track 268 for the time periods where no facial data was collected in that track. Other embodiments interpolate data for periods where no track includes facial data. In other embodiments, analysis includes interpolating mental state analysis when the mental state data collected is intermittent.

The mental state data, such as the continuous mental state data 230 and/or any of the collected facial data 240, 242, 244, 246, and 248 may be tagged. The tags may include metadata related to the mental state data, including, but not limited to, the device that collected the mental state data; the individual from whom the mental state data was collected; the task being performed by the individual; the media being viewed by the individual; and the location, environmental conditions, time, date, or any other contextual information. The tags may be used to locate pertinent mental state data; for example, the tags may be used to retrieve the mental state data from a database. The tags may be included with the mental state data that is sent over the internet to cloud or web-based storage and/or services so that the tags may be used locally on the machine where the mental state data was collected and/or remotely on a remote server or a cloud/web service.

Figure 3:
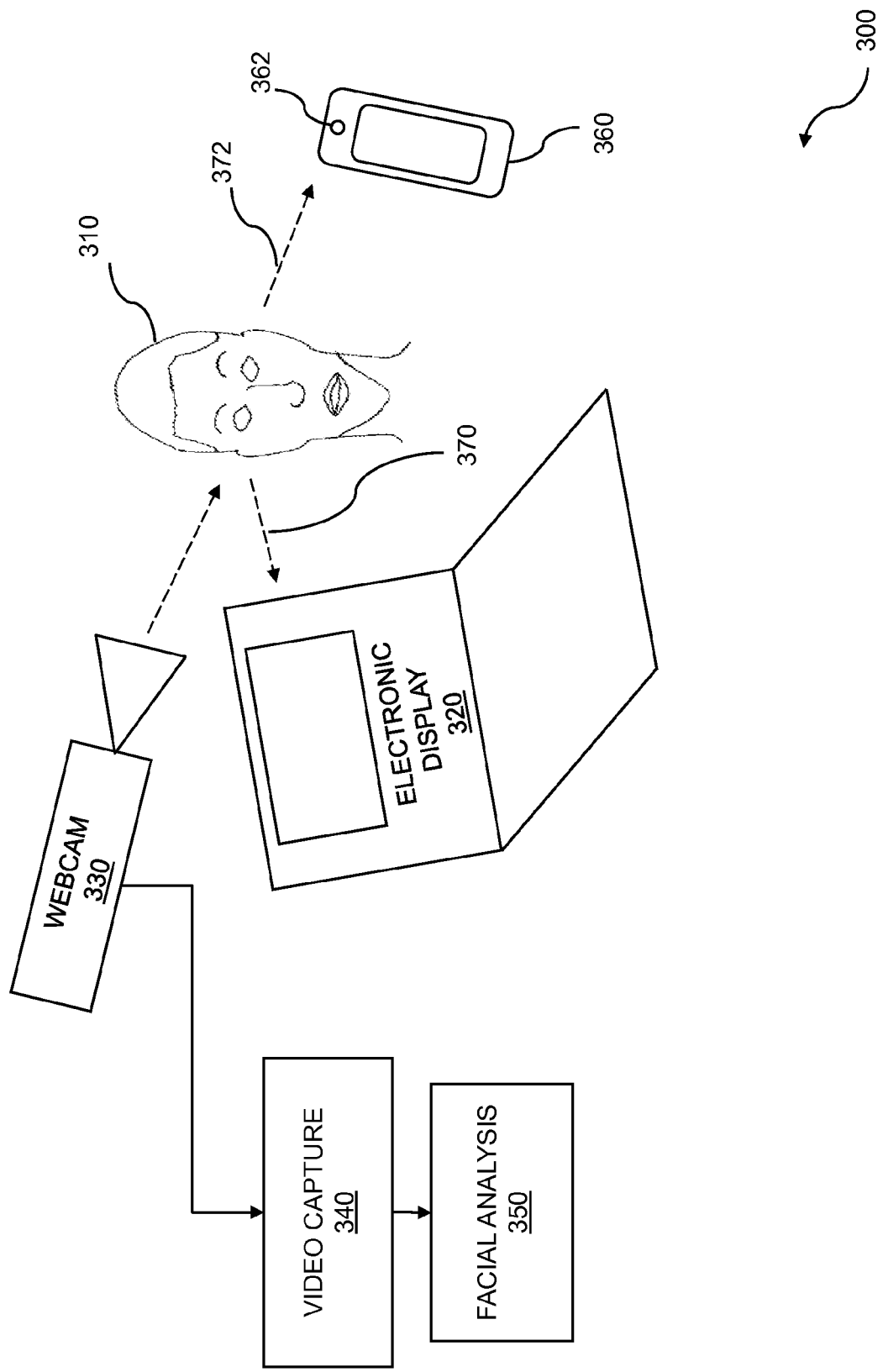
FIG. 3 is a diagram for facial analysis.

FIG. 3 is a diagram for facial analysis 300. An individual 310 may view 370 an electronic display 320 while mental state data on the individual 310 may be collected and analyzed. The electronic display 320 may show an output of a computer application that the individual 310 is using, or the electronic display 320 may show a media presentation in a manner which exposes the individual 310 to the media presentation. The media presentation may include one of a group consisting of a movie, a television show, a web series, a webisode, a video, a video clip, an electronic game, an e-book, or an e-magazine. The electronic display 320 may be a part of, or may be driven from, the device collecting the mental state data. Or, depending on the embodiment, the electronic display may only be loosely coupled to, or may be unrelated to, the device collecting the mental state data. The collecting, in some embodiments, is accomplished with a mobile device 360, such as a cell phone, a tablet computer, or a laptop computer, and the mobile device may include a forward facing camera 362 when the user views 372 the mobile device 360. The facial data may be collected with a camera such as the forward facing camera 362 of the mobile device 360 and/or by a webcam 330. The facial data may be collected intermittently when the individual 310 is looking in the direction of a camera 362/330. The camera may also capture images of the setting. These images may be used in determining contextual information.

The webcam 330 may be used to collect one or more of facial data and physiological data. The facial data may include, in various embodiments, information on facial expressions, action units, head gestures, smiles, smirks, brow furrows, squints, lowered eyebrows, raised eyebrows, or attention. The webcam 330 may capture video, audio, and/or still images of the individual 310. A webcam, as the term is used herein, may include a video camera, still camera, thermal imager, CCD device, phone camera, three-dimensional camera, a depth camera, multiple webcams used to show different views of a person, or any other type of image capture apparatus that may allow data captured to be used in an electronic system. The images of the person 310 from the webcam 330 may be captured by a video capture unit 340. In some embodiments, video may be captured, while in others, one or more still images may be captured. The captured video or still images may be used in facial analysis 350 or for determining gestures, actions, or other movements.

Analysis of facial expressions, gestures, and mental states may be accomplished using the captured images of the person 310. The facial expressions may be used to identify smiles, frowns, and other facial indicators of mental states. The gestures, including head gestures, may indicate interest or curiosity. For example, a head gesture of moving toward the electronic display 320 may indicate increased interest in the media or desire for clarification. Based on the captured images, analysis of physiological data may be performed. Respiration, heart rate, heart rate variability, perspiration, temperature, and other physiological indicators of mental state may be determined by analyzing the images.

Figure 4:
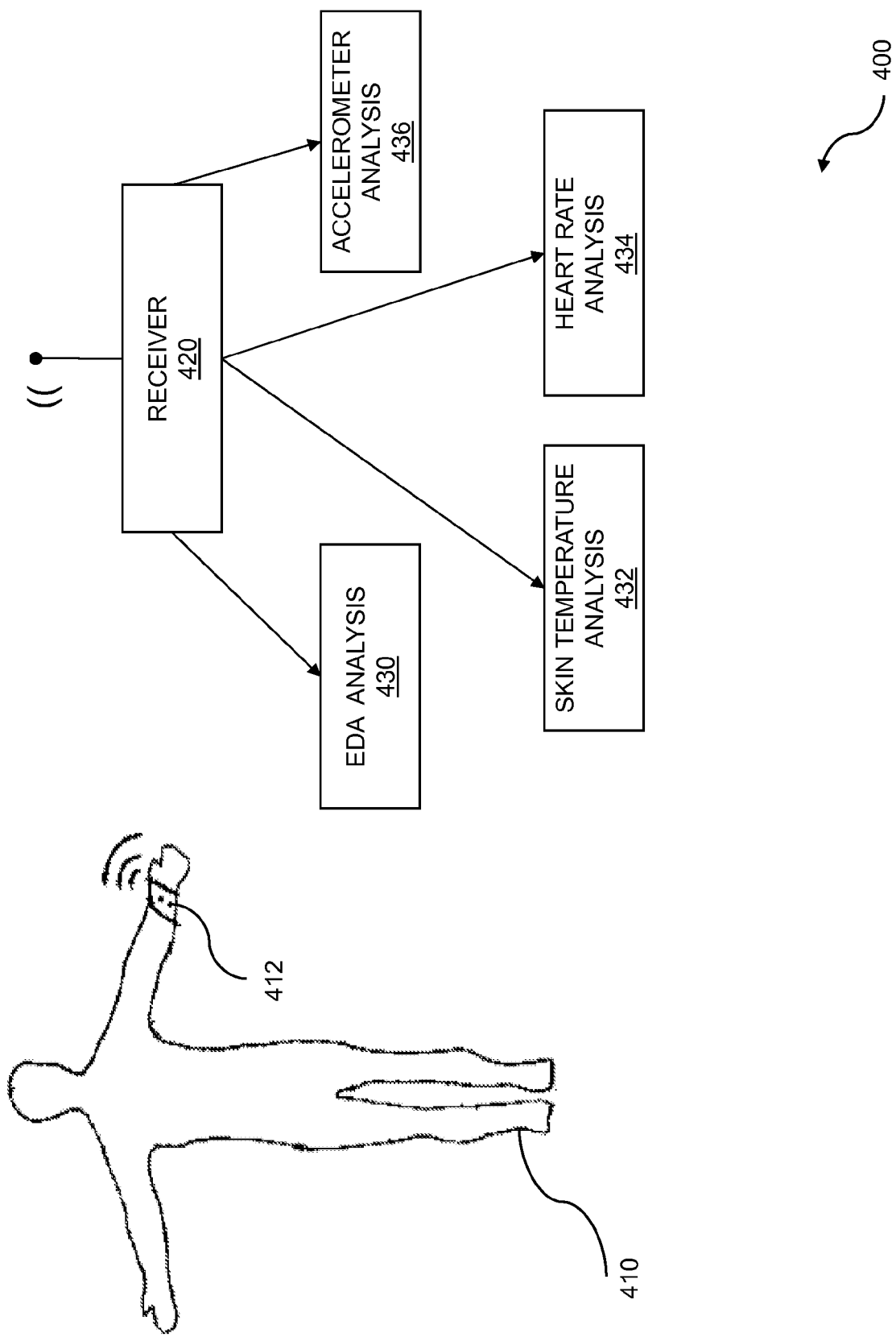
FIG. 4 is diagram for sensor analysis.

FIG. 4 is a diagram representing physiological analysis. A system 400 may analyze data collected from a person 410 as he or she interacts with a computer. The person 410 may have a biosensor 412 attached to him or her for the purpose of collecting mental state data. The biosensor 412 may be placed on the wrist, palm, hand, head, or other part of the body. In some embodiments, multiple biosensors may be placed on the body in multiple locations. The biosensor 412 may include detectors for physiological data such as electrodermal activity, skin temperature, accelerometer readings, and the like. Other detectors for physiological data may be included as well, such as heart rate, blood pressure, EKG, EEG, further brain waves, and other physiological detectors. The biosensor 412 may transmit information collected to a receiver 420 using wireless technology such as Wi-Fi, Bluetooth, 802.11, cellular, or other bands. In other embodiments, the biosensor 412 may communicate with the receiver 420 by other methods such as a wired interface or an optical interface. The receiver may provide the data to one or more components in the system 400. In some embodiments, the biosensor 412 may record multiple types of physiological information in memory for later download and analysis. In some embodiments, the download of recorded physiological data may be accomplished through a USB port or other wired or wireless connection.

Mental states may be inferred based on physiological data, such as physiological data from the sensor 412. Mental states may also be inferred based on facial expressions and head gestures observed by a webcam, or a combination of data from the webcam and data from the sensor 412. The mental states may be analyzed based on arousal and valence. Arousal can range from being highly activated—such as when someone is agitated—to being entirely passive—such as when someone is bored. Valence can range from being very positive—such as when someone is happy—to being very negative—such as when someone is angry. Physiological data may include one or more of electrodermal activity (EDA), heart rate, heart rate variability, skin temperature, respiration, accelerometer readings, and other types of analysis of a human being. It will be understood that both here and elsewhere in this document, physiological information can be obtained either by biosensor 412 or by facial observation via the webcam 330. Facial data may include facial actions and head gestures used to infer mental states. Further, the data may include information on hand gestures or body language and body movements such as visible fidgets. In some embodiments, these movements may be captured by cameras, while in other embodiments, these movements may be captured by sensor readings. Facial data may include the tilting the head to the side, leaning forward, smiling, frowning, and many other gestures or expressions.

Electrodermal activity may be collected in some embodiments. It may either be collected continuously, every second, four times per second, eight times per second, 32 times per second, or on some other periodic basis. Or, in some embodiments, electrodermal activity may be collected on an intermittent basis. The electrodermal activity may be recorded and stored onto a disk, a tape, flash memory, a computer system, or streamed to a server. The electrodermal activity may be analyzed 430 to indicate arousal, excitement, boredom, or other mental states based on observed changes in skin conductance. Skin temperature may be collected and/or recorded on a periodic basis. In turn, the skin temperature may be analyzed 432. Changes in skin temperature may indicate arousal, excitement, boredom, or other mental states. Heart rate may be collected and recorded, and may also be analyzed 434. A high heart rate may indicate excitement, arousal, or other mental states. Accelerometer data may be collected and used to track one, two, or three dimensions of motion. The accelerometer data may be recorded. The accelerometer data may be used to create an actigraph showing an individual's activity level over time. The accelerometer data may be analyzed 436 and may indicate a sleep pattern, a state of high activity, a state of lethargy, or other states. The various data collected by the biosensor 412 may be used along with the facial data captured by the webcam in the analysis of mental state. Contextual information may be based on one or more of skin temperature and/or accelerometer data.

Figure 5:
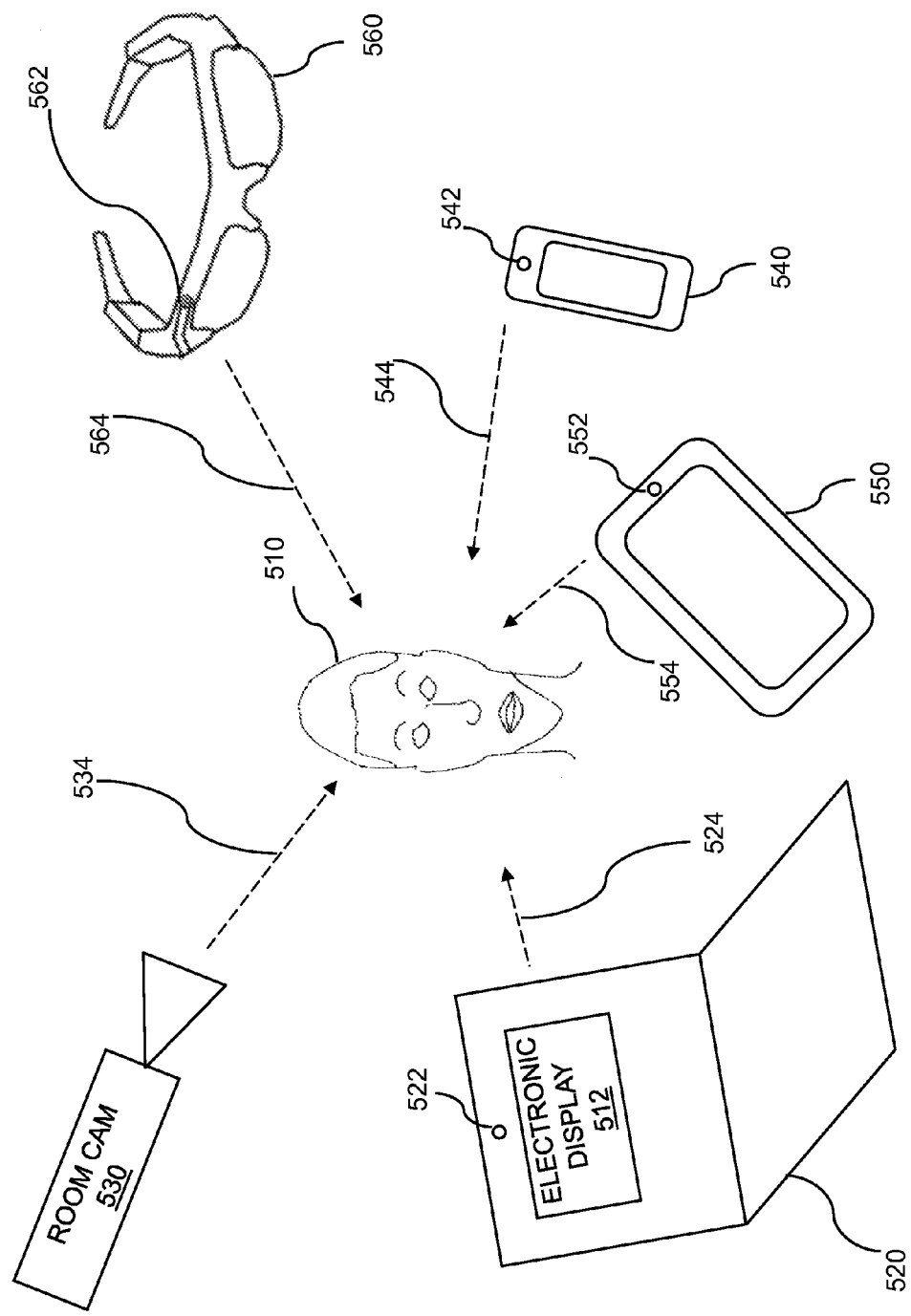
FIG. 5 is a diagram showing mental state data, including facial data, collection from multiple devices.

FIG. 5 is a diagram 500 showing mental state data, including facial data, collection from multiple devices. Mental state data can be collected sporadically from a group of different devices. A user 510 may be performing a task, viewing a media presentation on an electronic display 512, or doing something else where it may be useful to determine the user's mental state. The electronic display 512 may be on a laptop computer 520 as shown, a tablet computer 550, a cell phone 540, a desktop computer monitor, a television, or any other type of electronic device. The mental state data may be collected on a mobile device such as a cell phone 540, a tablet computer 550, or a laptop computer 520. Thus, the multiple sources may include at least one mobile device, such as a phone 540, a tablet 550, or a wearable device such as glasses 560. A mobile device may include a forward facing camera and/or rear facing camera that may be used to collect mental state data. The at least two sources of facial data may include one or more of a webcam 522, a phone camera 542, a tablet camera 552, a wearable camera 562, and a room camera 530. A wearable camera may be a wrist camera, a wristwatch camera, or other wearable camera device.

As the user 510 is monitored, the user 510 may move due to the nature of the task, boredom, distractions, or for another reason. As the user moves, the user's face may be visible from one or more of the multiple sources. Thus if the user 510 is looking in a first direction, the line of sight 524 from the webcam 522 may be able to observe the individual's face, but if the user is looking in a second direction, the line of sight 534 from the room camera 530 may be able to observe the individual's face. Further, if the user is looking in a third direction, the line of sight 544 from the phone camera 542 may be able to observe the individual's face. If the user is looking in a fourth direction, the line of sight 554 from the tablet camera 552 may be able to observe the individual's face. If the user is looking in a fifth direction, the line of sight 564 from the wearable camera 562 may be able to observe the individual's face. The wearable device such as the glasses 560 may be worn by another user or an observer. In other embodiments, the wearable device is a device other than glasses, such as an earpiece with a camera, a helmet or hat with a camera, a clip-on camera attached to clothing, or any other type of wearable device with a camera or other sensor for collecting mental state data. The individual 510 may also wear a wearable device including a camera that may be used for gathering contextual information and/or collecting mental state data on other users. Because the individual 510 may move their head, the facial data may be collected intermittently when the individual is looking in a direction of a camera. In some cases, multiple people may be included in the view from one or more cameras, and some embodiments include filtering out faces of one or more other people to determine whether the individual 510 is looking toward a camera. All or some of the mental state data can be sporadically available from these various devices.

Figure 6:
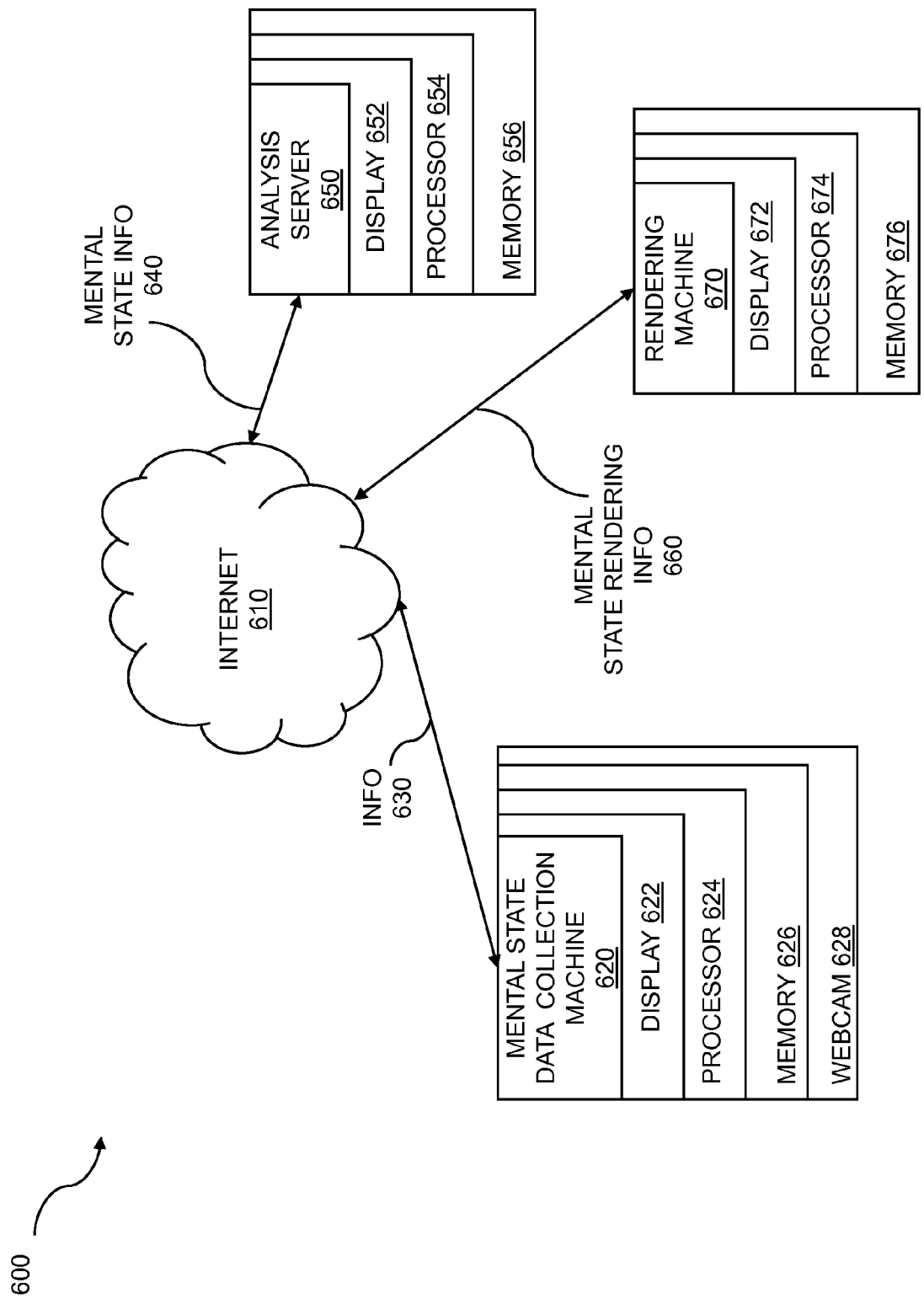
FIG. 6 is a system diagram for mental state analysis.

FIG. 6 is a system diagram for mental state analysis. A system 600 may include a mental state data collection machine 620 and an analysis server 650. The mental state data collection machine 620 may be configured to collect the mental state data of an individual on an intermittent basis. The mental state data collection machine 620 may include a display 622, one or more processors 624, a memory 626 designed to store mental state data, instructions, and the like, and a webcam 628. The display 622 may be any electronic display, including but not limited to, a computer display, a laptop screen, a net-book screen, a tablet computer screen, a cell phone display, a mobile device display, a remote with a display, a television, a projector, or the like. The webcam 628 may comprise a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that may allow image data captured to be used by an electronic system. The mental state data collection machine 620 may be configured to transmit mental state information 630 to a server 650 via the Internet 610 or other network.

The analysis server 650 may be configured to obtain analysis of the mental state data on the individual and render an output based on the analysis of the mental state data. The analysis server 650 may obtain mental state information 640 from the internet and may be configured as a web service. In some embodiments the analysis server 650 may send the analysis of the mental state data to another machine, such as the mental state data collection machine, so that the analysis of the mental state data may be received from a web service. The analysis server 650 may include a display 622, one or more processors 654, and a memory 656 designed to store system information, instructions, and the like. The display 652 may be any electronic display, including but not limited to, a computer display, a laptop screen, a net-book screen, a tablet computer screen, a cell phone display, a mobile device display, a remote with a display, a television, a projector, or the like. The one or more processors 654, when executing the instructions which are stored, may be configured to analyze mental state information 640 that may be received from the mental state data collection machine 620. In some embodiments, the mental state data collection machine 620 and the analysis server 650 functions may be combined into a single computer. In some embodiments, the rendering of mental state analysis can occur on a different computer than the collection machine 620 or the analysis server 650. This computer may be a rendering machine 670 which receives data or information 630, mental state information 640 from the analysis machine 650, or both and may be considered mental state rendering information 660. In embodiments, the rendering machine 670 includes one or more processors 674 coupled to a memory 676, and a display 672. The rendering may include generation and display of emoticons.

The system 600 may include computer program product comprising code for collecting mental state data of an individual on an intermittent basis, code for obtaining analysis of the mental state data on the individual, and code for rendering an output based on the analysis of the mental state data. A computer-implemented method for mental state analysis, from a server perspective, may comprise receiving mental state data collected from an individual on an intermittent basis, analyzing the mental state data from the individual, and sending an output related to analyzing that was performed.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, mobile device, tablet, wearable computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
    collecting mental state data of an individual on an intermittent basis;
    collecting other mental state data, including electrodermal activity data, from the individual on a continuous basis;
    obtaining analysis of the mental state data on the individual, as a result of sending a request to a web service for the analysis where the analysis of the mental state data is received from the web service;
    interpolating, using one or more processors, mental state analysis in between the collecting which is intermittent;
    imputing additional mental state data where the mental state data is missing;
    filtering out faces of one or more other people to determine when an individual is looking in a direction of a camera;
    determining contextual information based on accelerometer data; and
    rendering an output based on the analysis of the mental state data.

2. The method of claim 1 further comprising interpolating mental state data in between the collecting which is intermittent.

3. The method of claim 1 further comprising collecting other mental state data from the individual on a continuous basis.

4. The method of claim 1 wherein the collecting of the mental state data is accomplished with a mobile device.

5. The method of claim 1 wherein the collecting of the mental state data is accomplished for one type of mental state data.

6. The method of claim 5 wherein the one type of mental state data includes facial data.

7. The method of claim 6 wherein the facial data is collected with a webcam.

8. The method of claim 6 wherein the facial data is collected intermittently when the individual is looking in a direction of a camera.

9. The method of claim 8 further comprising performing face detection to determine when the individual is looking in the direction of the camera.

10. The method of claim 8 further comprising filtering out faces of one or more other people to determine when the individual is looking in the direction of the camera.

11. The method of claim 1 further comprising determining contextual information.

12. The method of claim 1 further comprising sending one or more of the mental state data, a subset of the mental state data, or an initial analysis of the mental state data to the web service.

13. The method of claim 1 wherein the mental state data includes one or more of smiles, laughter, smirks, or grimaces.

14. The method of claim 1 further comprising posting the analysis to a social network.

15. A computer program product embodied in a non-transitory computer readable medium for mental state analysis, the computer program product comprising:
    code for collecting mental state data of an individual on an intermittent basis;
    code for collecting other mental state data, including electrodermal activity data, from the individual on a continuous basis;
    code for obtaining analysis of the mental state data on the individual, as a result of sending a request to a web service for the analysis where the analysis of the mental state data is received from the web service;
    code for interpolating, using one or more processors, mental state analysis in between the collecting which is intermittent;
    code for imputing additional mental state data where the mental state data is missing;
    code for filtering out faces of one or more other people to determine when an individual is looking in a direction of a camera;
    code for determining contextual information based on accelerometer data; and
    code for rendering an output based on the analysis of the mental state data.

16. A system for mental state analysis comprising:
    a memory for storing instructions;
    one or more processors attached to the memory wherein the one or more processors are configured to:
        collect mental state data of an individual on an intermittent basis;
        collect other mental state data, including electrodermal activity data, from the individual on a continuous basis;
        obtain analysis of the mental state data on the individual, as a result of sending a request to a web service for the analysis where the analysis of the mental state data is received from the web service;
        interpolate, using one or more processors, mental state analysis in between the collecting which is intermittent;
        impute additional mental state data where the mental state data is missing;

filter out faces of one or more other people to determine when an individual is looking in a direction of a camera;
determine contextual information based on accelerometer data; and
render an output based on the analysis of the mental state data.

17. The computer program product of claim 15 further comprising code for interpolating mental state data in between the collecting which is intermittent.

18. The computer program product of claim 15 further comprising code for collecting other mental state data from the individual on a continuous basis.

19. The computer program product of claim 15 wherein the collecting of the mental state data accomplished for one type of mental state data.

20. The computer program product of claim 19 wherein the one type of mental state data includes facial data.

21. The computer program product of claim 15 wherein the mental state data includes one or more of smiles, laughter, smirks, or grimaces.

22. The computer program product of claim 15 further comprising code for posting the analysis to a social network.

\* \* \* \* \*